(12) United States Patent
Motohara et al.

(10) Patent No.: US 10,362,929 B2
(45) Date of Patent: Jul. 30, 2019

(54) IMAGING UNIT, IMAGING MODULE, AND ENDOSCOPE

(71) Applicant: OLYMPUS CORPORATION, Tokyo (JP)

(72) Inventors: Hiroyuki Motohara, Hachioji (JP); Yasuhiro Kusano, Fukushima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/799,290

(22) Filed: Oct. 31, 2017

(65) Prior Publication Data

US 2018/0049628 A1 Feb. 22, 2018

Related U.S. Application Data

(63) Continuation of application No. PCT/JP2017/002064, filed on Jan. 23, 2017.

(30) Foreign Application Priority Data

Jan. 28, 2016 (JP) .................................. 2016-014338

(51) Int. Cl.
*A61B 1/05* (2006.01)
*H01L 27/14* (2006.01)
(Continued)

(52) U.S. Cl.
CPC ............ *A61B 1/05* (2013.01); *A61B 1/00114* (2013.01); *A61B 1/051* (2013.01);
(Continued)

(58) Field of Classification Search
CPC .... A61B 1/05; A61B 1/00114; H04N 5/2253; H04N 2005/2255
(Continued)

(56) References Cited

U.S. PATENT DOCUMENTS

| 2006/0164533 A1* | 7/2006 | Hsieh | ................ H01L 27/14632 348/317 |
| 2012/0257852 A1* | 10/2012 | Ogawa | ................ G02B 6/4201 385/14 |
| 2014/0055587 A1* | 2/2014 | Saito | ................... A61B 1/00105 348/75 |

FOREIGN PATENT DOCUMENTS

| JP | 63-240825 A | 10/1988 |
| JP | 2005-278760 A | 10/2005 |

(Continued)

OTHER PUBLICATIONS

International Search Report dated Mar. 7, 2017 in PCT/JP2017/002064.
Decision to Grant a Patent dated Jun. 6, 2017 in 2017-522998.

*Primary Examiner* — Mehrdad Dastouri
*Assistant Examiner* — Kristin Dobbs
(74) *Attorney, Agent, or Firm* — Scully, Scott, Murphy & Presser, P.C.

(57) ABSTRACT

An imaging unit includes: a semiconductor package including an image sensor and a connection electrode; a circuit board including a main body including a connection land, and an attachment portion protruding on a back surface of the main body and including cable connection electrodes formed on at least two opposing side surfaces; electronic components mounted on an electronic component mounting area on the back surface; and cables electrically and mechanically connected to the cable connection electrodes of the attachment portion. The attachment portion protrudes from the main body such that a center plane of the two side surfaces is shifted from a center plane of side surfaces parallel to the two side surfaces, and at least one side surface is perpendicular to the back surface of the main body. The electronic component mounting area is arranged on the back (Continued)

surface of the main body side-by-side with the attachment portion.

11 Claims, 15 Drawing Sheets

(51) Int. Cl.
    *H04N 5/369*     (2011.01)
    *A61B 1/00*     (2006.01)
    *H04N 5/225*     (2006.01)
    *G02B 23/24*     (2006.01)

(52) U.S. Cl.
    CPC .......... *G02B 23/2484* (2013.01); *H01L 27/14* (2013.01); *H04N 5/2253* (2013.01); *H04N 5/369* (2013.01); *H04N 2005/2255* (2013.01)

(58) Field of Classification Search
    USPC .......................................................... 348/75
    See application file for complete search history.

(56) References Cited

FOREIGN PATENT DOCUMENTS

| | | |
|---|---|---|
| JP | 2006-314582 A | 11/2006 |
| JP | 2014-000314 A | 1/2014 |
| JP | 2015-062555 A | 4/2015 |

\* cited by examiner

FIG.8
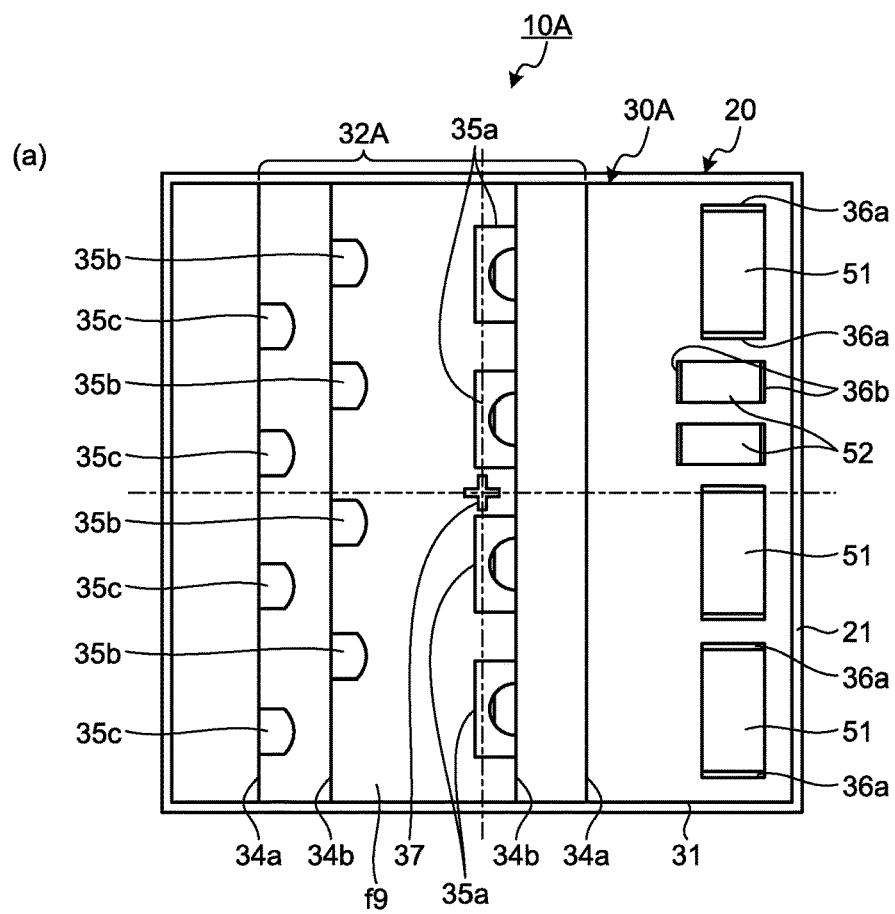
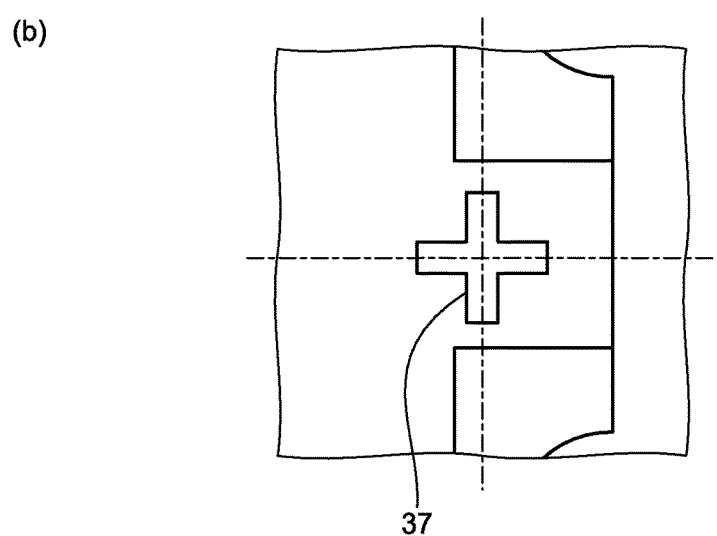

IMAGING UNIT, IMAGING MODULE, AND ENDOSCOPE

CROSS-REFERENCE TO RELATED APPLICATION

This application is a continuation of PCT international application Ser. No. PCT/JP2017/002064 filed on Jan. 23, 2017 which designates the United States, incorporated herein by reference, and which claims the benefit of priority from Japanese Patent Applications No. 2016-014338, filed on Jan. 28, 2016, incorporated herein by reference.

BACKGROUND

The present disclosure relates to an imaging unit, an imaging module, and an endoscope.

In the related art, endoscope apparatuses are widely used for various examinations in medical and industrial fields. Among these, medical endoscope apparatuses are widely used because its capability of obtaining in-vivo images inside the body cavity of a subject such as a patient without performing incision on the subject by inserting in the body cavity of the subject a flexible insertion section having an elongated shape including an image sensor provided at its distal end, and its capability of further performing treatment procedure by allowing a treatment instrument to be projected from the distal end of the insertion section as necessary.

At the distal end of the insertion section of such an endoscope apparatus, an imaging unit including an image sensor and a circuit board on which electronic components such as a capacitor and an IC chip constituting a drive circuit of the image sensor are mounted is fitted, with signal cables being soldered to the circuit board of the imaging unit.

In recent years, there is proposed an imaging unit in which the circuit board to be connected to the image sensor has a three-dimensional structure, with electronic components mounted on the back surface, or the like, of the circuit board, having signal cables connected to a side surface of the circuit board for the purpose of simplifying connection work of signal lines of a cable, enhancing reliability of the connection portion, or for miniaturization (for example, refer to JP 2014-314 A).

SUMMARY

An imaging unit may include: a semiconductor package including an image sensor, and a connection electrode formed on a back surface; a circuit board including a main body including a connection land formed on a front surface, the connection land being electrically and mechanically connected to the connection electrode via a bump, and an attachment portion protruding on a back surface of the main body and including cable connection electrodes formed on at least two opposing side surfaces among protruding side surfaces; a plurality of electronic components mounted on an electronic component mounting area on the back surface of the main body of the circuit board; and a plurality of cables electrically and mechanically connected to the cable connection electrodes of the attachment portion, wherein the attachment portion protrudes from the main body such that a center plane of the two side surfaces on which the cable connection electrodes are formed to oppose each other is shifted from a center plane of side surfaces parallel to the two side surfaces of the attachment portion of the semiconductor package, and at least one side surface is perpendicular to the back surface of the main body, and the electronic component mounting area is arranged on the back surface of the main body side-by-side with the attachment portion.

The above and other objects, features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 8 is a top view of an imaging unit according to a first modification of the first embodiment in a state where no cables are connected;

DETAILED DESCRIPTION

Figure 1:
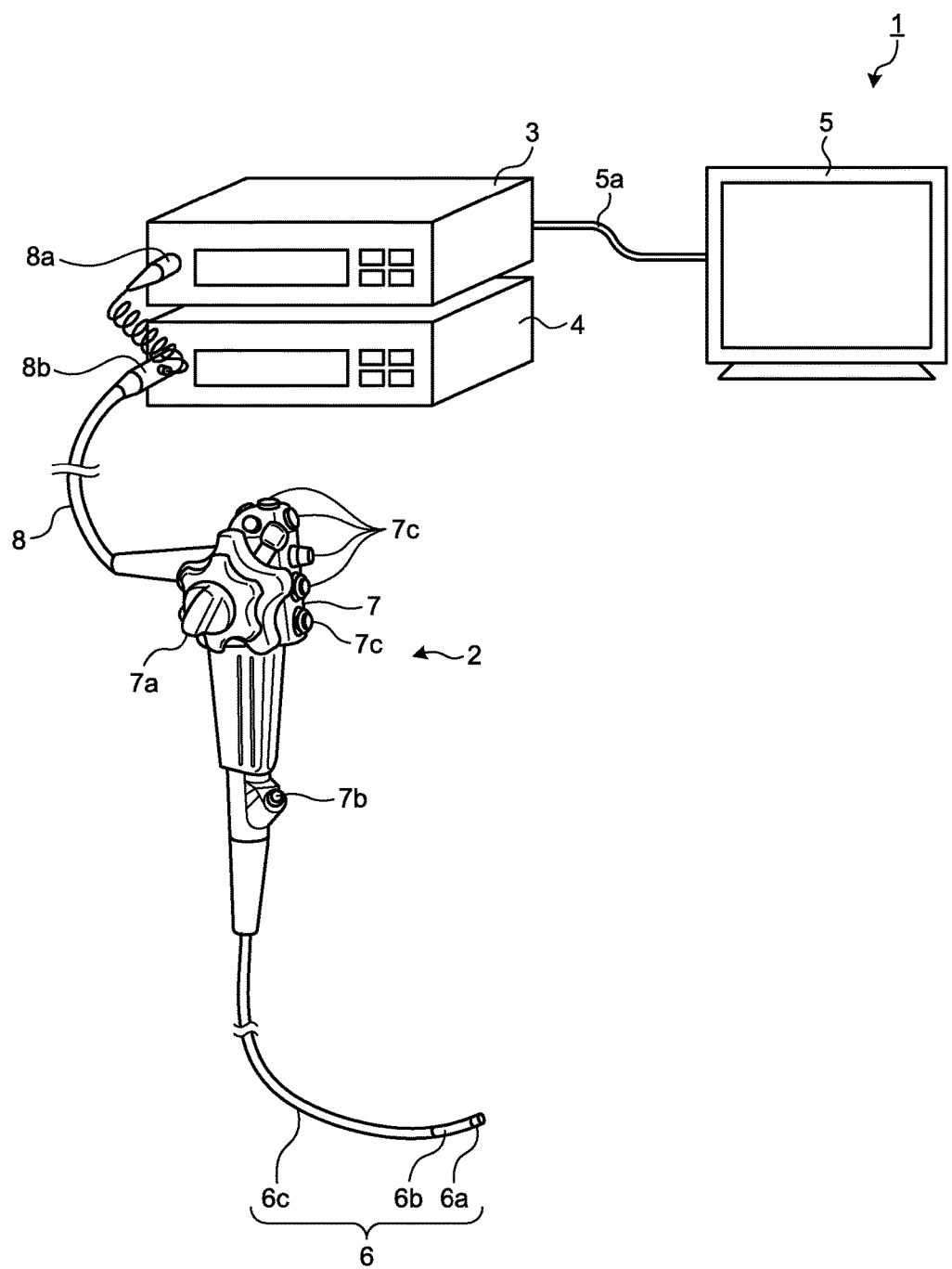
FIG. 1 is a block diagram schematically illustrating an overall configuration of an endoscope system according to a first embodiment.

Hereinafter, an endoscope system including an imaging unit will be described according to embodiments (hereinafter, referred to as "embodiment(s)"). Note that the present disclosure is not intended to be limited by these embodiments. In the drawings, same reference signs are attached to the same portions. Furthermore, it needs to be kept in mind that the drawings are schematic, and the relationship between the thickness and the width of individual members and the ratio between the members are different from an actual case. Still further, there are portions having different dimensions and ratios even between the drawings.

First Embodiment

FIG. 1 is a block diagram schematically illustrating an overall configuration of an endoscope system according to a first embodiment. As illustrated in FIG. 1, an endoscope system 1 according to the first embodiment includes an endoscope 2, an information processing apparatus 3, a light source apparatus 4, and a display device 5. The endoscope 2 is introduced into a subject and captures an image inside the body of a subject and generates an image signal of the interior of the subject. The information processing apparatus 3 performs predetermined image processing on the image signal captured by the endoscope 2 and controls each of portions of the endoscope system 1. The light source apparatus 4 generates illumination light for the endoscope 2. The display device 5 displays an image of the image signal after undergoing image processing by the information processing apparatus 3.

The endoscope 2 includes an insertion section 6, an operating unit 7, and a universal cord 8. The insertion section 6 is inserted into the subject. The operating unit 7 is arranged on a proximal end side of the insertion section 6 and gripped by an operator. The universal cord 8 has flexibility and extends from the operating unit 7.

The insertion section 6 is formed with an illumination fiber (light guide cable), an electric cable, an optical fiber, or the like. The insertion section 6 includes a distal end portion 6a, a bending portion 6b, and a flexible tube portion 6c. The distal end portion 6a includes an imaging unit described below. The bending portion 6b is a bendable portion formed with a plurality of bending pieces. The flexible tube portion 6c is flexible and provided on a proximal end side of the bending portion 6b. The distal end portion 6a includes an illumination unit, an observation unit, an opening portion, and an air/water feeding nozzle (not illustrated). The illumination unit illuminates an interior of the subject via an illumination lens. The observation unit captures the interior of the subject. The opening portion communicates with a treatment instrument channel.

The operating unit 7 includes a bending knob 7a, a treatment instrument insertion section 7b, and a plurality of switching sections 7c. The bending knob 7a is used to bend the bending portion 6b in up-down and left-right directions. The treatment instrument insertion section 7b is a section through which a treatment instrument such as biological forceps and a laser knife is inserted into the body cavity of the subject. Each of the switching sections 7c is used to operate peripheral equipment such as the information processing apparatus 3, the light source apparatus 4, an air feeding apparatus, a water feeding apparatus, and a gas feeding apparatus. A treatment instrument inserted from the treatment instrument insertion section 7b passes through an internal treatment instrument channel and comes out from the opening portion of the distal end of the insertion section 6.

The universal cord 8 includes an illumination fiber and a cable. The universal cord 8 is branched at a proximal end. One end portion of the branched section is a connector 8a, and the other proximal end is a connector 8b. The connector 8a is removably attached to the connector of the information processing apparatus 3. The connector 8b is removably attached to the light source apparatus 4. The universal cord 8 transmits illumination light emitted from the light source apparatus 4 to the distal end portion 6a via the connector 8b and the illumination fiber. Moreover, the universal cord 8 transmits an image signal captured by an imaging unit to be described below to the information processing apparatus 3 via the cable and the connector 8a.

The information processing apparatus 3 performs predetermined image processing on the image signal output from the connector 8a, while controlling the whole endoscope system 1.

The light source apparatus 4 is configured with a light source that emits light, a condenser lens, or the like. Under the control of the information processing apparatus 3, the light source apparatus 4 emits light from the light source and supplies the light to the endoscope 2 connected via the connector 8b and the illumination fiber of the universal cord 8, as illumination light supplied to the interior of the subject as an object.

The display device 5 includes a display using liquid crystal or organic electro luminescence (EL). The display device 5 displays, via a video cable 5a, various types of information including an image that has undergone predetermined image processing performed by the information processing apparatus 3. With this configuration, the operator may observe a desired position inside the subject and judge conditions by operating the endoscope 2 while viewing an image (in-vivo image) displayed by the display device 5.

Figure 2:
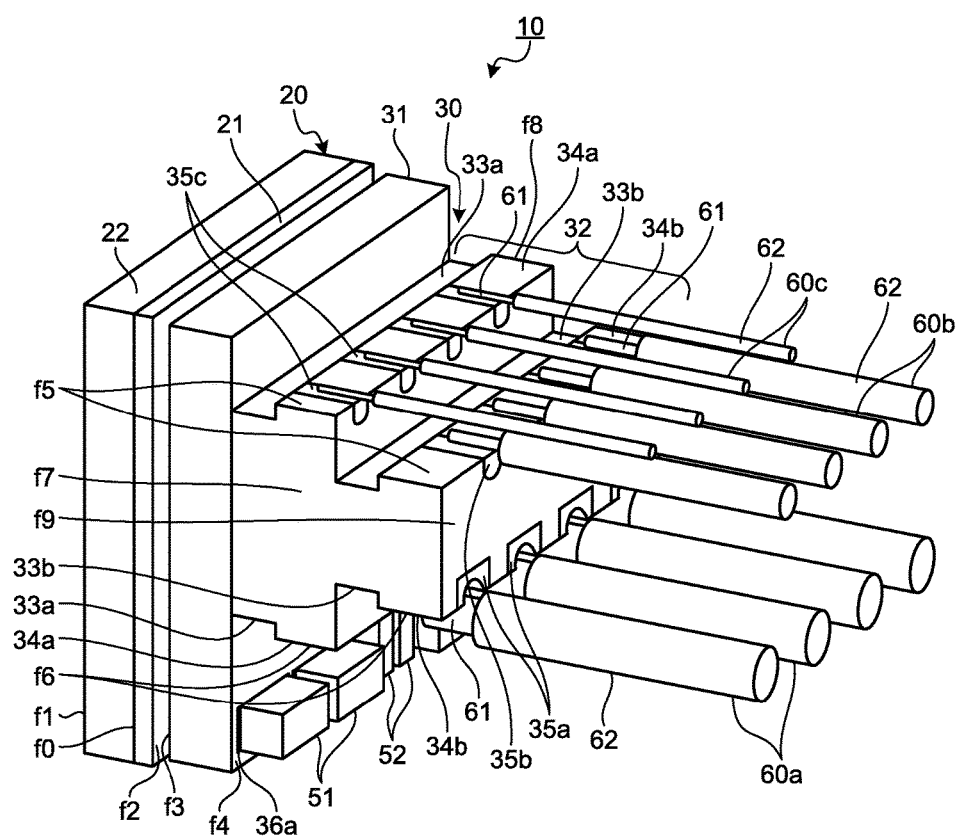
FIG. 2 is a perspective view of an imaging unit arranged at a distal end portion of the endoscope illustrated in FIG. 1.
Figure 3:
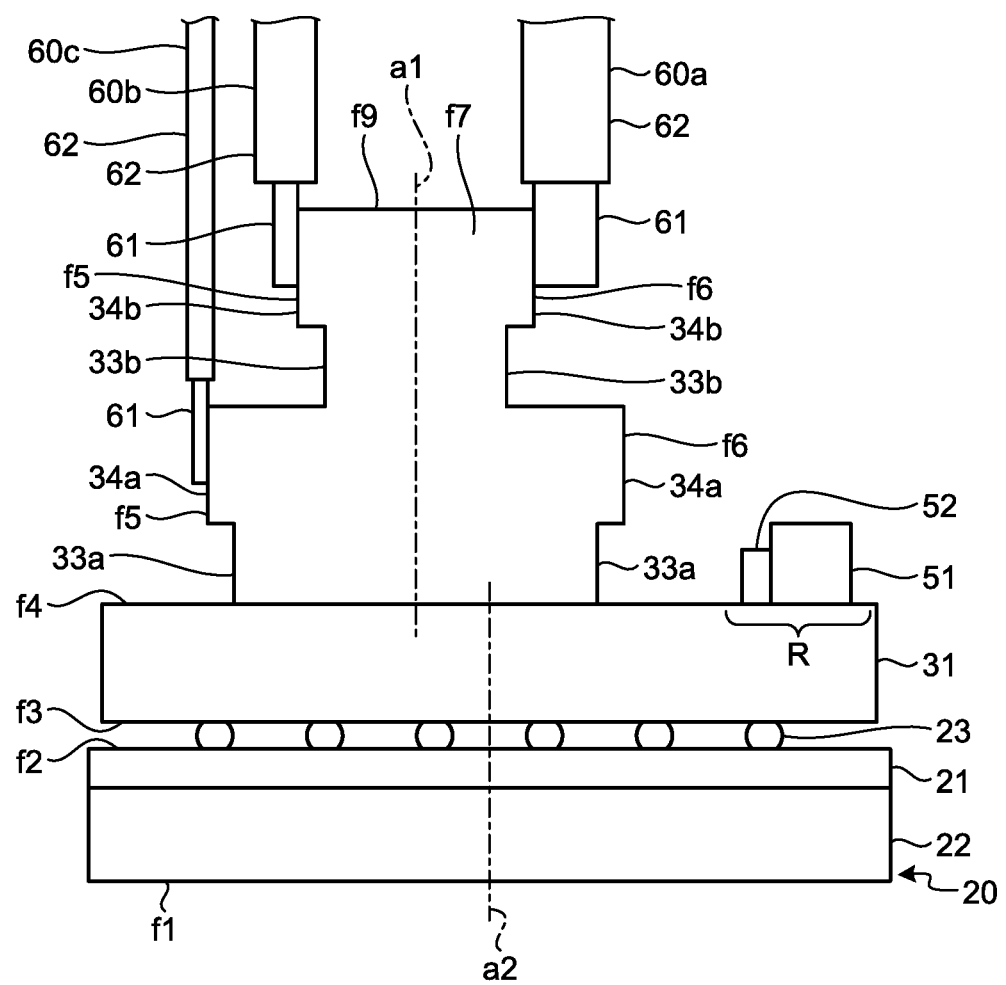
FIG. 3 is a side view of the imaging unit illustrated in FIG. 2.
Figure 4:
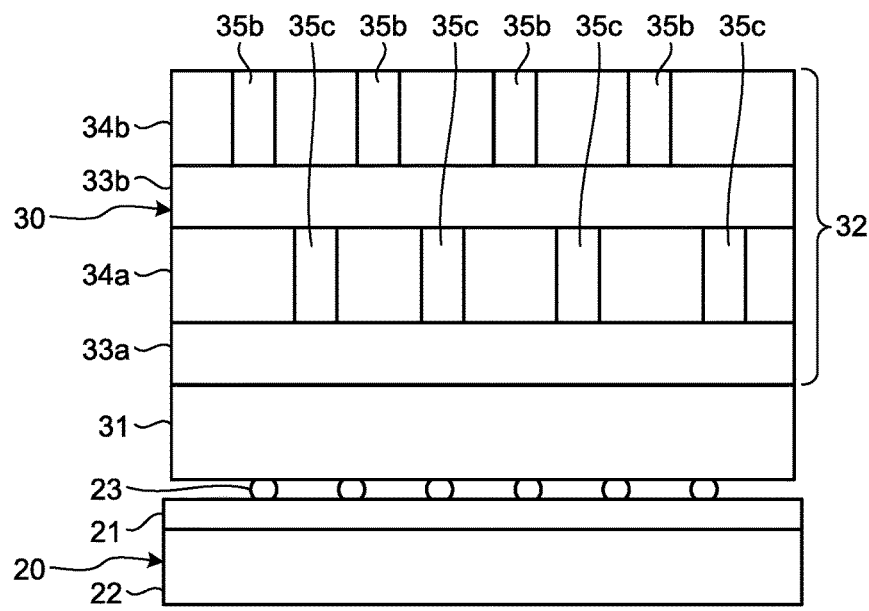
FIG. 4 is a side view of the imaging unit illustrated in FIG. 2 in a state where no cables are connected.
Figure 5:
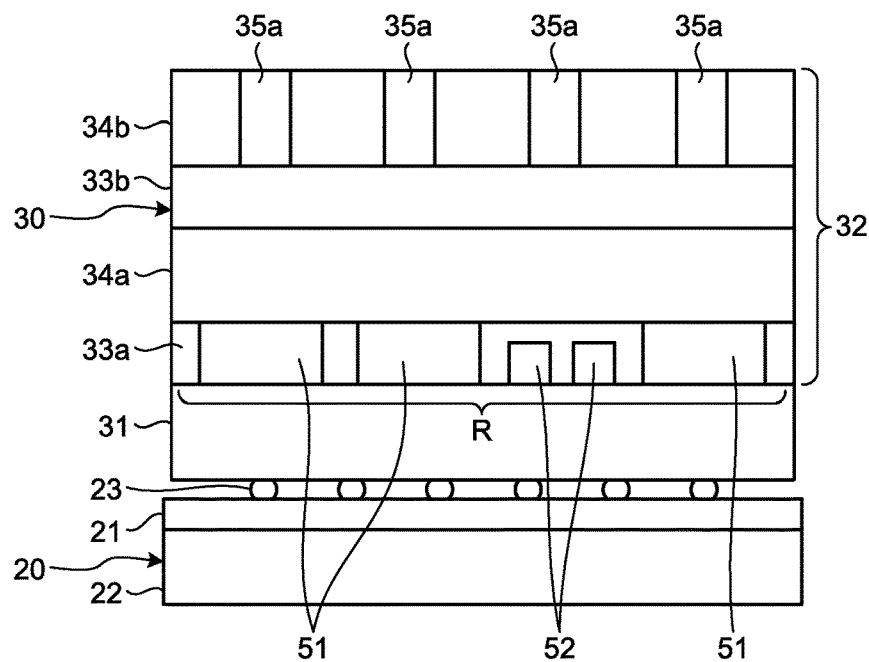
FIG. 5 is a side view (opposite side of FIG. 4) of the imaging unit illustrated in FIG. 2 in a state where no cables are connected.
Figure 6:
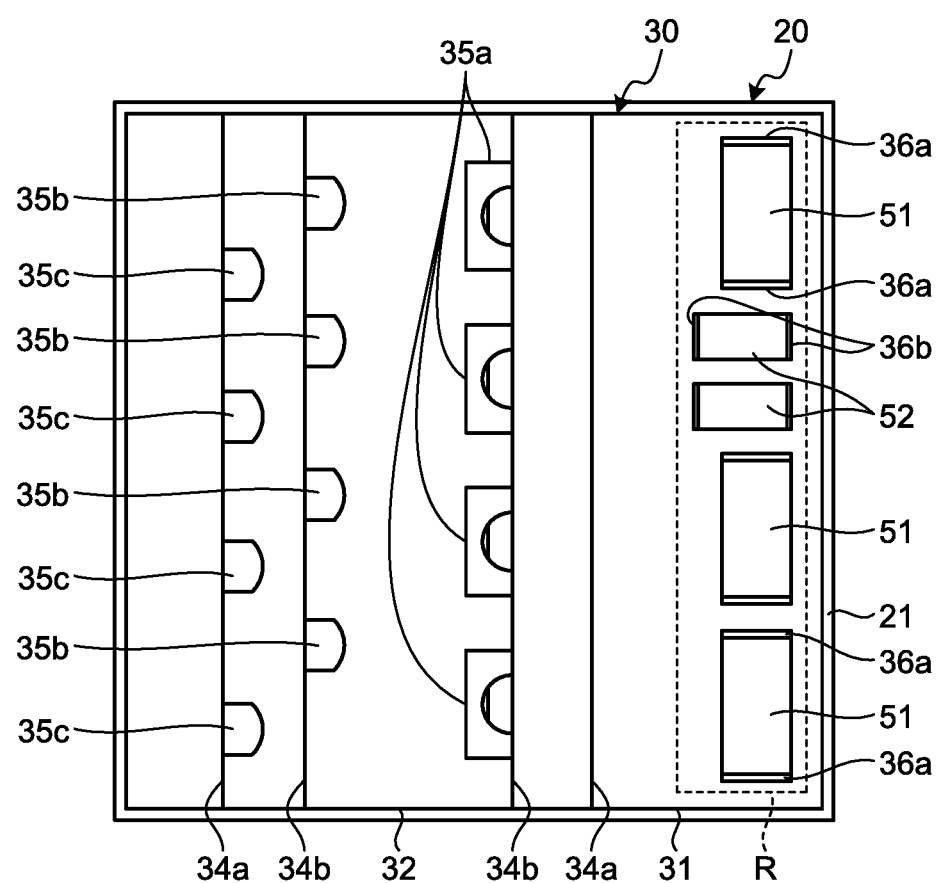
FIG. 6 is a top view of the imaging unit illustrated in FIG. 2 in a state where no cables are connected.
Figure 7:
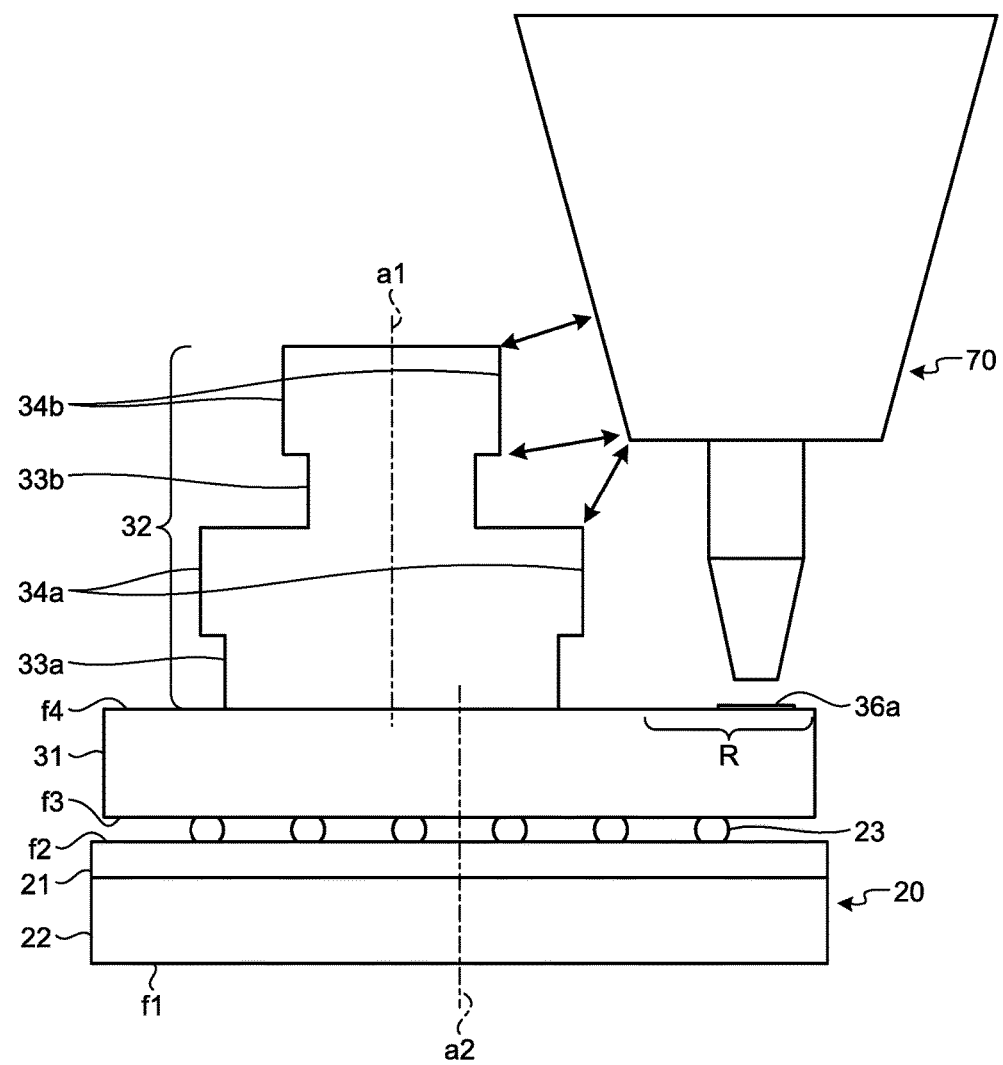
FIG. 7 is a diagram for explaining supply of solder to a circuit board using a dispenser needle.

Next, the imaging unit used in the endoscope system 1 will be described in detail. FIG. 2 is a perspective view of the imaging unit arranged at the distal end portion of the endoscope 2 illustrated in FIG. 1. FIG. 3 is a side view of the imaging unit illustrated in FIG. 2. FIG. 4 is a side view of the imaging unit illustrated in FIG. 2 in a state where no cables are connected. FIG. 5 is a side view (opposite side of FIG. 4) of the imaging unit illustrated in FIG. 2 in a state where no cables are connected. FIG. 6 is a top view of the imaging unit illustrated in FIG. 2 in a state where no cables are connected. FIG. 7 is a diagram for explaining supply of solder to a circuit board using a dispenser needle. Note that FIGS. 2 to 7 omit illustration of an underfill agent filled between a semiconductor package 20 and a circuit board 30 and the solder used for connecting cables 60a to 60c and electronic components 51 and 52.

An imaging unit 10 includes a semiconductor package 20, a circuit board 30, a plurality of electronic components 51 and 52, and a plurality of cables 60a, 60b, and 60c. The semiconductor package 20 includes an image sensor 21 and has a connection electrode formed on a back surface f2. The circuit board 30 includes a main body 31 and an attachment portion 32. The main body 31 has a connection land electrically and mechanically connected to the connection electrode formed on a front surface f3 via a bump 23. The attachment portion 32 protrudes onto a back surface f4 of the main body 31. Cable connection electrodes 35a, 35b and 35c are formed on opposing side surfaces f5 and f6 among the side surfaces protruding from the back surface f4 of the main body 31. The plurality of electronic components 51 and 52 is mounted in an electronic component mounting area R on the back surface f4 of the main body 31 of the circuit board 30. The plurality of cables 60a, 60b and 60c is electrically and mechanically connected to the cable connection electrodes 35a, 35b and 35c of the attachment portion 32.

The semiconductor package 20 has a structure in which glass 22 is attached to the image sensor 21. The light condensed by a lens unit passes through a surface f1 which is a front surface of the glass 22 and enters a surface f0 (light receiving surface) of the image sensor 21 having a light receiving portion. Connection electrodes (not illustrated) and the bump 23 formed of solder, or the like, are formed on the surface f2 (back surface) of the image sensor 21. It is preferable that the semiconductor package 20 is a chip size package (CSP) formed by performing wiring, electrode formation, resin encapsulation, and dicing on an image sensor chip in a wafer state, and that the size of the image sensor chip finally becomes the size of the semiconductor package chip.

The circuit board 30 is a multi-layer substrate formed with a plurality of stacked substrates with wiring being formed (a plurality of stacked substrates parallel to the front surface f3 and the back surface f4), and includes the plate-like main body 31 and the attachment portion 32 protruding in a step shape. Examples of the stacked substrate include a ceramic substrate, a glass epoxy substrate, a flexible substrate, a glass substrate, and a silicon substrate. The main body 31 and the attachment portion 32 may be an integrated substrate or a combination of separately manufactured substrates. The attachment portion 32 and the electronic component mounting area R are arranged side-by-side on the back surface f4 of the main body 31. The electronic component mounting area R is arranged closer to one side of the main body 31. Examples of the electronic components 51 and 52 to be mounted include passive components such as capacitors and resistive coils and active components such as a driver IC. While in the first embodiment, as illustrated in FIGS. 5 and 6, three electronic components 51 and two electronic components 52 are mounted, the types and the number of electronic components 51 and 52 to be mounted are not limited to this.

The attachment portion 32 includes a first step portion 34a and a second step portion 34b formed on each of the side surfaces f5 and f6, from the side closer to the main body 31. The cable connection electrode 35c connecting the cable 60c is formed on the side surface f5 opposing the side surface f6 on the side of the electronic component mounting area R of the first step portion 34a. The cable connection electrodes 35a and 35b connecting the cables 60a and 60b, respectively, are formed on the side surfaces f5 and f6 of the second step portion 34b.

As illustrated in FIGS. 4 and 6, the cable connection electrodes 35b and 35c formed on the side of the side surface f5 are arranged in a staggered lattice pattern (zigzag shape). Moreover, the cable connection electrodes 35a and 35b formed to be opposing each other on the second step portion 34b are also arranged in a staggered lattice pattern (zigzag shape). By arranging the cable connection electrodes 35a to 35c in a staggered lattice pattern (zigzag shape), it is possible to increase the mounting density of the cables 60a to 60c.

As illustrated in FIG. 3, the attachment portion 32 is formed integrally with the main body 31 such that the attachment portion 32 protrudes from the main body 31 in a state where a center plane a1 of the side surfaces f5 and f6 on which the cable connection electrodes 35a and 35b are formed to be opposing each other shifts (shifting to the left side in FIG. 3) from a center plane a2 of side surfaces parallel to the side surfaces f5 and f6 of the attachment portion 32 of the semiconductor package 20. With this arrangement, it is possible to use a portion closer to one side on the back surface f4 of the main body 31 as the electronic component mounting area R. As illustrated in FIG. 7, solder is supplied to a mounting land 36a with a dispenser needle 70 when the electronic components 51 and 52 are mounted on the mounting land 36a of the main body 31. In the first embodiment, the electronic component mounting area R is arranged side-by-side with the attachment portion 32 on a portion closer to one side on the back surface f4 of the main body 31. With this arrangement, it is possible to supply the solder accurately from above without generating interference of the dispenser needle 70 with the attachment portion 32, in particular, with the first step portion 34a and the second step portion 34b when the solder is supplied using the dispenser needle 70, making it possible to mount the electronic components 51 and 52 with high accuracy and simplicity.

Moreover, in a case where the electronic components 51 and 52 include a capacitor (decoupling capacitor), it is possible to arrange the decoupling capacitor in the immediate vicinity of the image sensor 21 via the main body 31 close to the image sensor 21. This makes it possible to reduce the impedance between the image sensor 21 and the decoupling capacitor, and to achieve stable driving of the image sensor 21 while increasing the speed of the image sensor 21.

Grooves 33a and 33b are provided at a portion between the main body 31 and the first step portion 34a and at a portion between the first step portion 34a and the second step portion 34b. Arrangement of the grooves 33a and 33b makes it possible to prevent the solder from flowing when the cables 60a to 60c are connected to the cable connection electrodes 35a to 35c, respectively, achieving the reduction of the risk of short circuit, or the like.

Each of the cables 60a, 60b, and 60c includes a conductor 61 and an outer casing 62 formed of an insulator for covering the conductor 61, with the outer casing 62 peeled off at the end portion to expose the conductor 61. The exposed conductor 61 is connected to the cable connection electrodes 35a, 35b, and 35c.

Among the cables 60a to 60c, the cable 60a has the largest diameter and the cable 60c has the smallest diameter. It is preferable to connect the cable 60c having a small diameter to the cable connection electrode 35c formed in the first step portion 34a, and preferable to connect the cable 60a having a large diameter to the cable connection electrodes 35a and 35b formed in the second step portion 34b. This makes it easier for the cables 60a to 60c connected to the circuit board 30 and the cable connection electrodes 35a to 35c to be accommodated within a projection plane in the optical axis direction of the semiconductor package 20.

While the cable 60a having a large diameter may be connected to any of the cable connection electrodes 35a and 35b formed in the second step portion 34b, the cable 60a is connected to the cable connection electrode 35a in the first embodiment. Connecting the cable 60a having a large diameter to the cable connection electrode 35a close to the center plane in the optical axis direction of the imaging unit 10 makes it possible to reduce the force applied to the imaging unit 10, generated by connecting the cables 60a to 60c to the cable connection electrodes 35a to 35c.

In the imaging unit 10 according to the first embodiment, the attachment portion 32 connecting the cables 60a to 60c is shifted from the center of the main body 31, thereby allowing the vacant space formed by the shifting to be used as the electronic component mounting area R. This enables accurate supply of the solder from above the electronic component mounting area R, making it possible to mount the electronic components 51 and 52 with high accuracy and simplicity. Moreover, by providing the first step portion 34a and the second step portion 34b on the side surfaces f5 and f6 of the attachment portion 32, it is possible to increase the mounting density of the cables 60a to 60c. Furthermore, the cable 60a having a large diameter is connected to the cable connection electrode 35a close to the center plane in the optical axis direction of the imaging unit 10, making it possible to reduce the force applied to the imaging unit 10, generated by connecting the cables 60a to 60c to the cable connection electrodes 35a to 35c.

Figure 9:
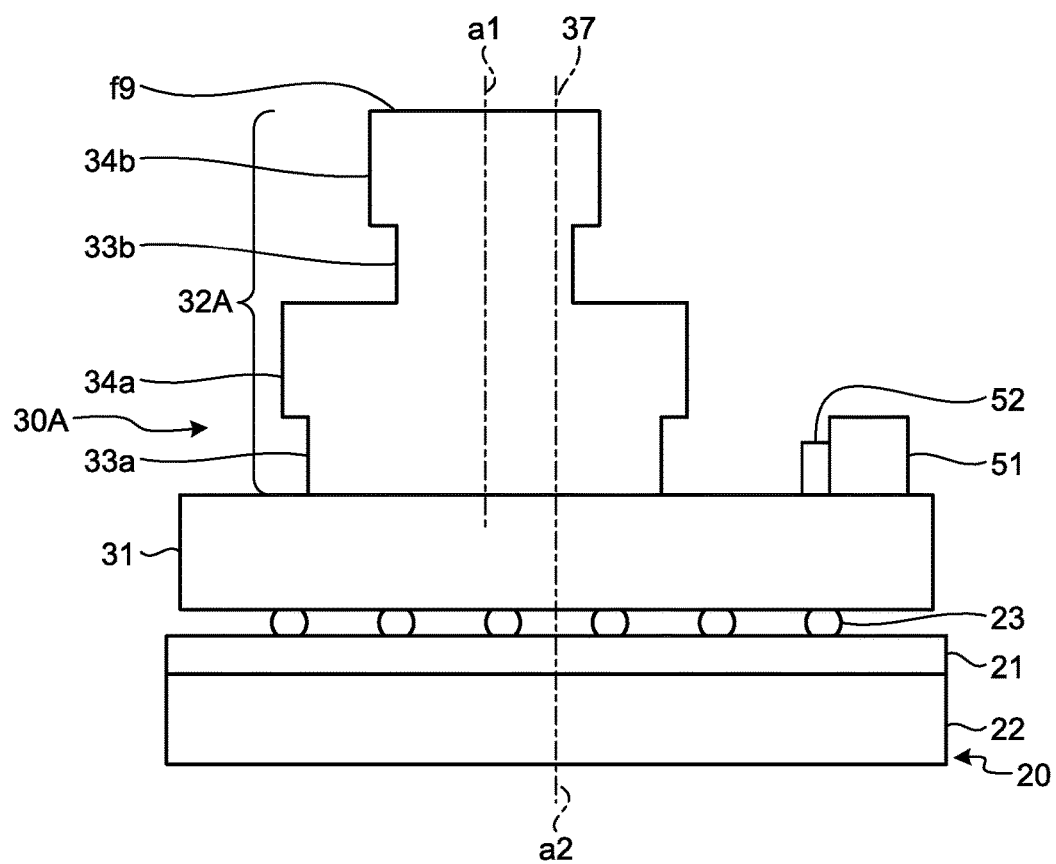
FIG. 9 is a side view of the imaging unit illustrated in FIG. 8.

Note that it is possible to provide a marker 37 on a back surface f9 of the attachment portion 32. FIG. 8 is a top view of an imaging unit 10A according to a first modification of the first embodiment in a state where no cables are connected. FIG. 9 is a side view of the imaging unit 10A illustrated in FIG. 8.

Figure 10:
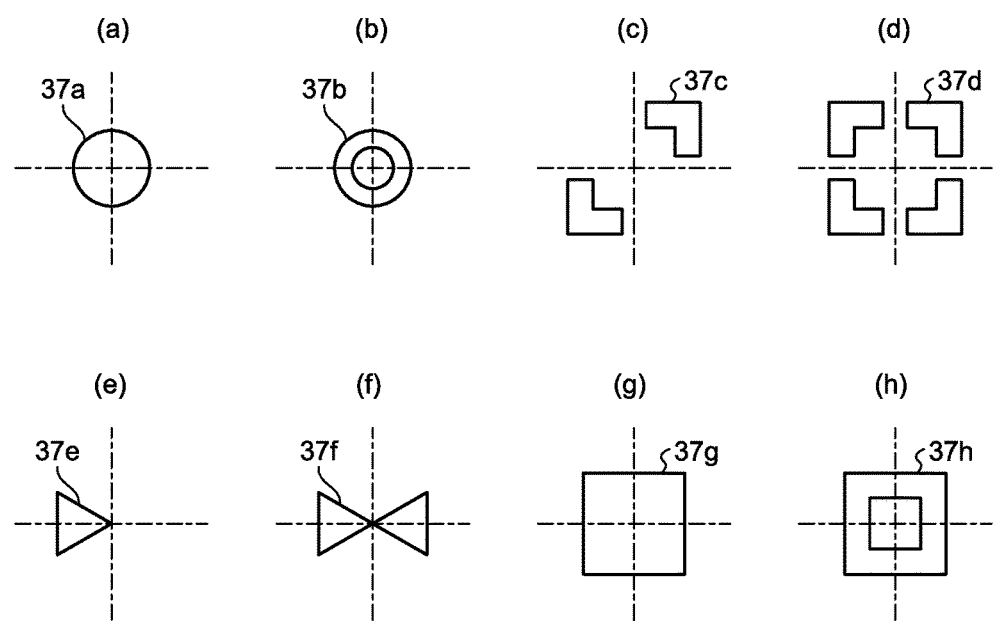
FIG. 10 is a diagram illustrating another shape of a marker.

In the imaging unit 10A according to the first modification, the marker 37 indicating the center position of the semiconductor package 20 is provided on the back surface f9 of an attachment portion 32A. In the imaging unit 10A, the semiconductor package 20 and the circuit board 30A are aligned with each other and thereafter are electrically and mechanically connected with each other via the bump 23. By arranging the marker 37 indicating the center position of the semiconductor package 20 on the back surface f9 of the attachment portion 32A, it is possible to facilitate alignment with the semiconductor package 20, leading to enhanced connection accuracy. While the marker 37 according to the first modification adopts a cross shape, the shape is not limited to this as long as the center position of the semiconductor package 20 may be visually recognized by its shape. For example, shapes such as markers 37a, 37b, 37c, 37d, 37e, 37f, 37g, and 37h illustrated in FIG. 10 may also be adopted.

Second Embodiment

Figure 11:
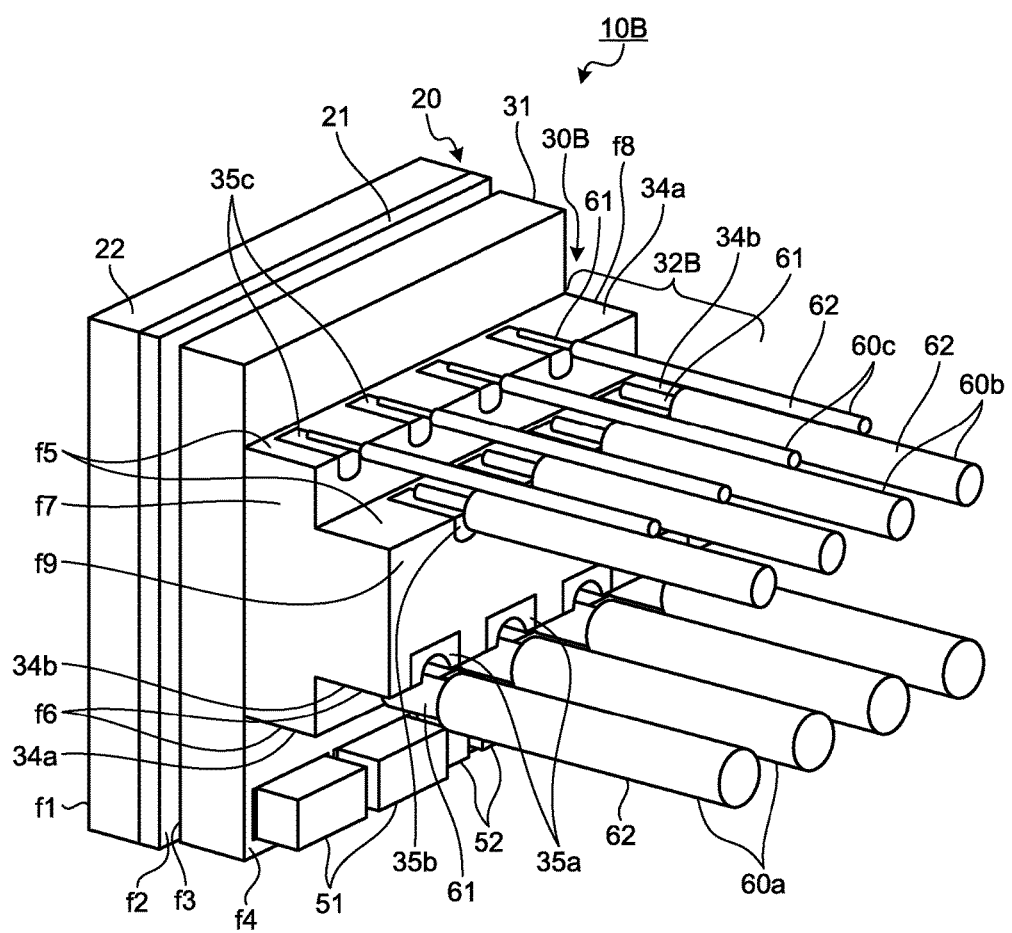
FIG. 11 is a perspective view of an imaging unit according to a second embodiment.
Figure 12:
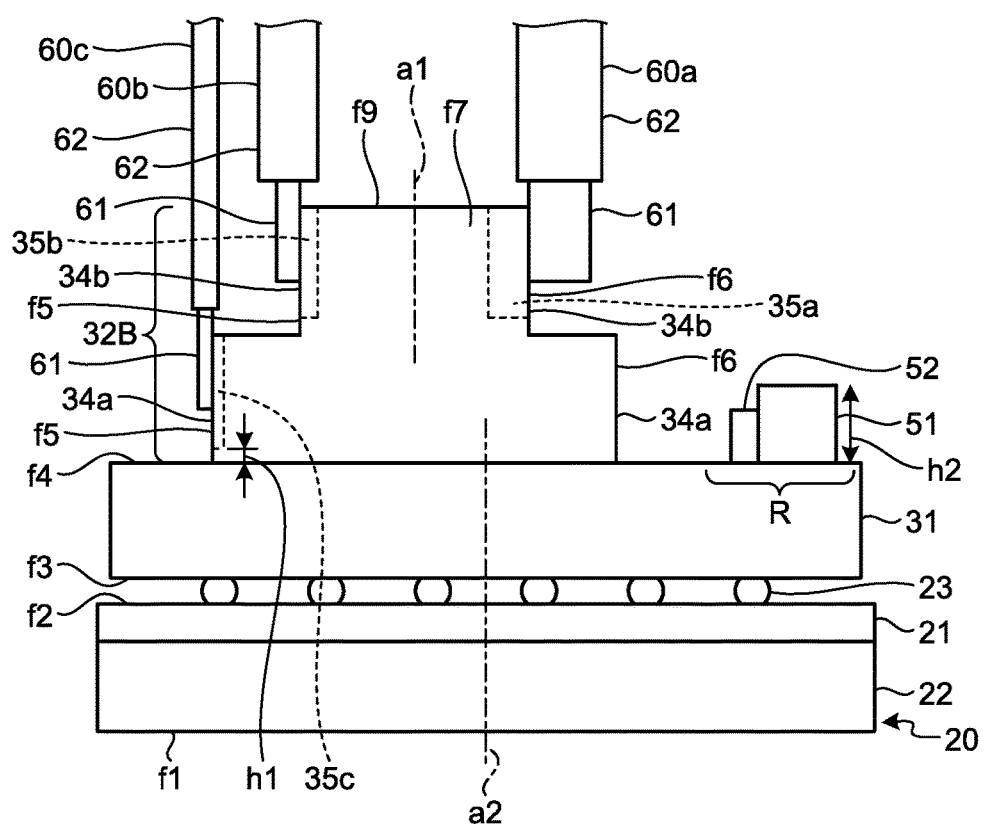
FIG. 12 is a side view of the imaging unit illustrated in FIG. 11.

An imaging unit 10B according to a second embodiment differs from the case of the first embodiment in that it does not have a groove at a portion between the main body 31 and the first step portion 34a and at a portion between the first step portion 34a and the second step portion 34b. FIG. 11 is a perspective view of the imaging unit 10B according to the second embodiment. FIG. 12 is a side view of the imaging unit 10B illustrated in FIG. 11. Note that FIGS. 11 and 12 omit illustration of an underfill agent filled between the semiconductor package 20 and a circuit board 30B and the solder used for connecting the cables 60a to 60c and the electronic components 51 and 52.

In the imaging unit 10B, no grooves are formed at a portion between the main body 31 and the first step portion 34a and at a portion between the first step portion 34a and the second step portion 34b. Since no grooves are formed, the length of an attachment portion 32B in the optical axis direction is reduced, making it possible to reduce the length of hard portions of the imaging unit 10B. Moreover, since no grooves are formed, it is possible to reduce the number of molds needed for manufacturing the circuit board 30B. With this configuration, it is possible provide an inexpensive endoscope with a smaller curvature R of the distal end portion when the imaging unit 10B is used in an endoscope.

The cable connection electrode 35c formed in the first step portion 34a is formed to be separated from the main body 31 and the cable connection electrodes 35a and 35b formed in the second step portion 34b are formed to be separated from the first step portion 34a. The cable connection electrode 35c formed in the first step portion 34a is arranged so as to overlap with the electronic components 51 and 52 in the optical axis direction. Overlapping with the electronic components 51 and 52 in the optical axis direction means that a length h1 from the main body 31-side end portion of the cable connection electrode 35c to the main body 31 is shorter than a height h2 of the electronic component 51. By forming the cable connection electrodes 35a to 35c to be separated from the main body 31 or the first step portion 34a, it is possible to reduce the risk of a short circuit or the like, due to the flow of the solder. Moreover, the length of the attachment portion 32B in the optical axis direction is reduced by arranging the cable connection electrode 35c so as to overlap with the electronic components 51 and 52 in the optical axis direction.

Moreover, similarly to the first embodiment, in the imaging unit 10B, the attachment portion 32B that connects the cables 60a to 60c is shifted from the center of the main body 31 so as to be arranged side-by-side with the electronic component mounting area R. With this configuration, it is possible to accurately supply the solder from above the electronic component mounting area R and to mount the electronic components 51 and 52 with high accuracy and simplicity. Moreover, the first step portion 34a and the second step portion 34b are provided on the side surfaces f5 and f6 of the attachment portion 32B, making it possible to increase the mounting density of the cables 60a to 60c. Furthermore, the cable 60a having a large diameter is connected to the cable connection electrode 35a close to the center plane in the optical axis direction of the imaging unit 10B, making it possible to reduce the force applied to the imaging unit 10B, generated by connecting the cables 60a to 60c to the cable connection electrodes 35a to 35c.

Third Embodiment

Figure 13:
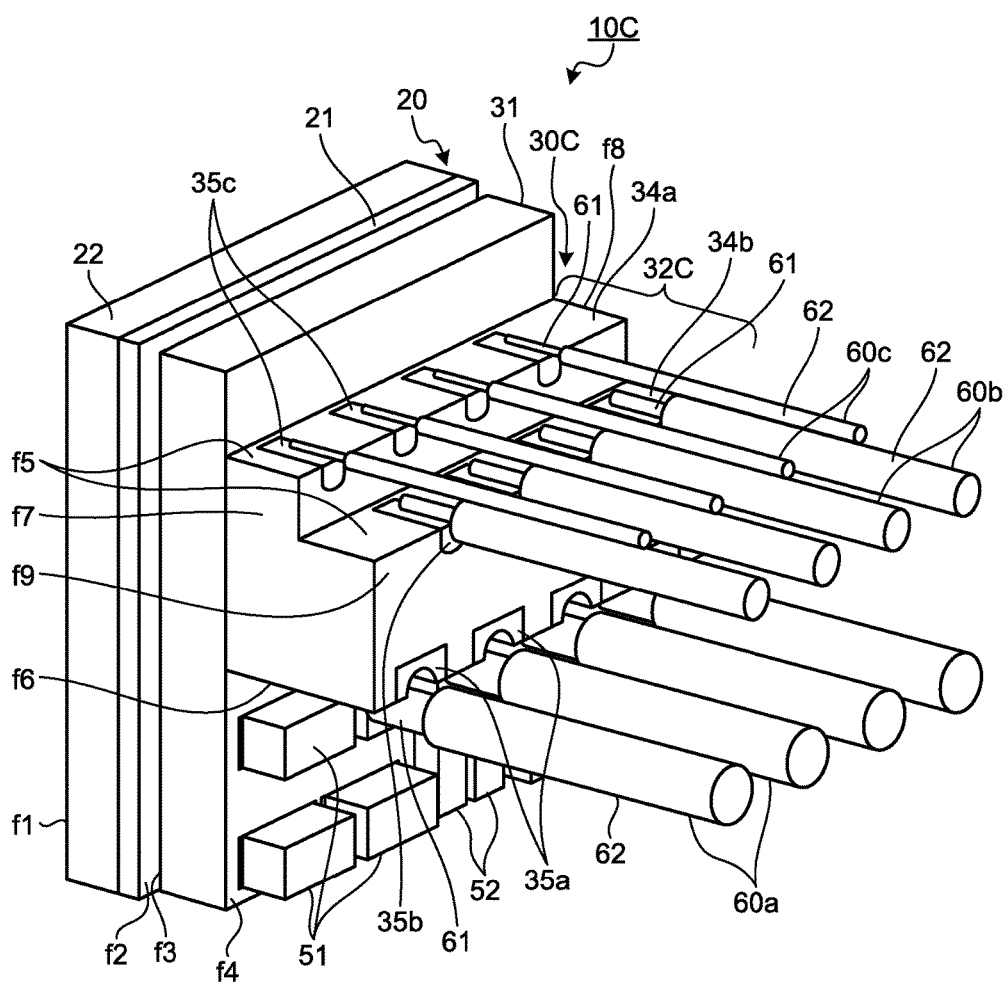
FIG. 13 is a perspective view of an imaging unit according to a third embodiment.
Figure 14:
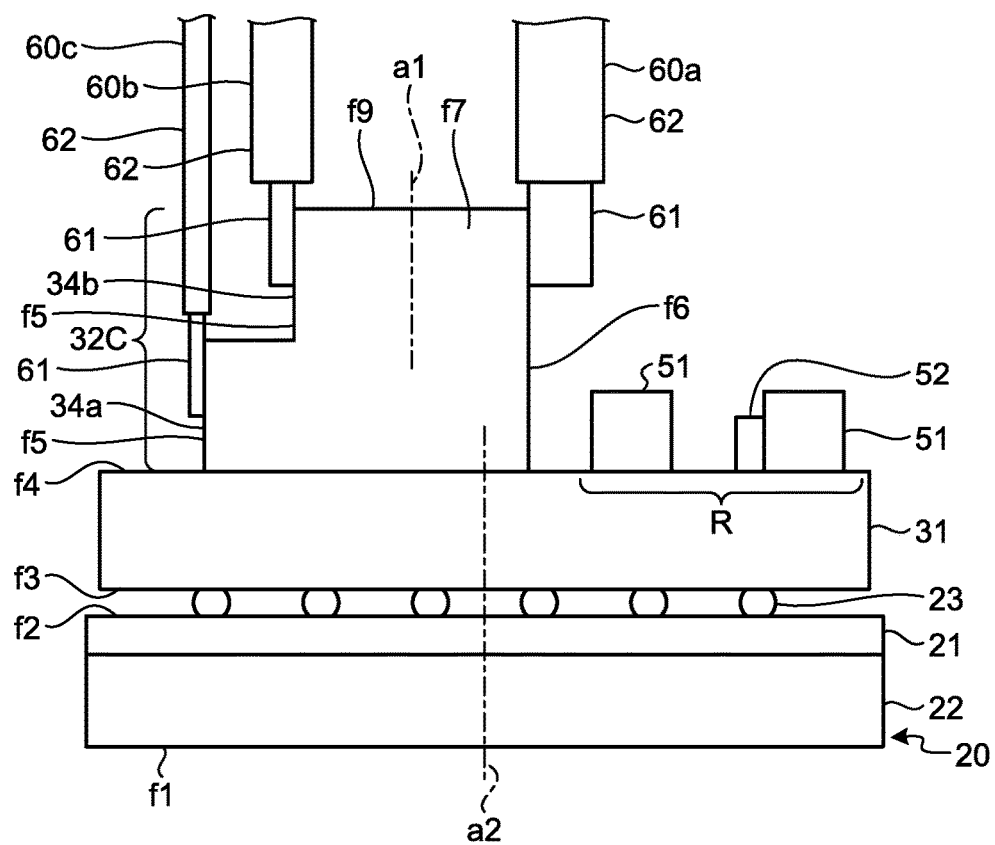
FIG. 14 is a side view of the imaging unit illustrated in FIG. 13.

An imaging unit 10C according to a third embodiment differs from the case of the first embodiment in that no step portion is formed on the side surface of an attachment portion 32C on the electronic component mounting area R side. FIG. 13 is a perspective view of the imaging unit 10C according to the third embodiment. FIG. 14 is a side view of the imaging unit 10C illustrated in FIG. 13. Note that FIGS. 13 and 14 omit illustration of an underfill agent filled between the semiconductor package 20 and a circuit board 30C and the solder used for connecting the cables 60a to 60c and the electronic components 51 and 52.

In the imaging unit 10C, the attachment portion 32C includes the first step portion 34a and the second step portion 34b formed solely on the side surface f5 from the side closer to the main body 31. A side surface f6 of the attachment portion 32C is a surface perpendicular to the back surface f4 of the main body 31. The cable connection electrodes 35c and 35b connecting the cables 60c and 60b, respectively, are formed on the side surface f5-side first step portion 34a and the second step portion 34b. The cable connection electrode 35a connecting the cable 60a is formed on a position opposing the cable connection electrode 35b, on the side surface f6.

In the imaging unit 10C, the attachment portion 32C is arranged such that the center plane a1 of the side surfaces f5 and f6 on which the cable connection electrodes 35a and 35b are formed is shifted from the center plane a2 of the side surfaces parallel to the side surfaces f5 and f6 of the attachment portion 32C of the semiconductor package 20, and in addition, no step portion is provided on the side surface f6 on the electronic component mounting area R side. With this configuration, it is possible to increase the electronic component mounting area R. This allows more electronic components 51 and 52 to be mounted, making it possible to provide the imaging unit 10C having high functionality. Moreover, since the first step portion 34a and the second step portion 34b are provided on the side surface f5 of the attachment portion 32C, it is possible to increase the mounting density of the cables 60a to 60c. Furthermore, by connecting the cable 60a having a large diameter to the cable connection electrode 35a close to the center plane in the optical axis direction of the imaging unit 10C, it is possible to reduce the force applied to the imaging unit 10C generated by connecting the cables 60a to 60c to the cable connection electrodes 35a to 35c.

Figure 15:
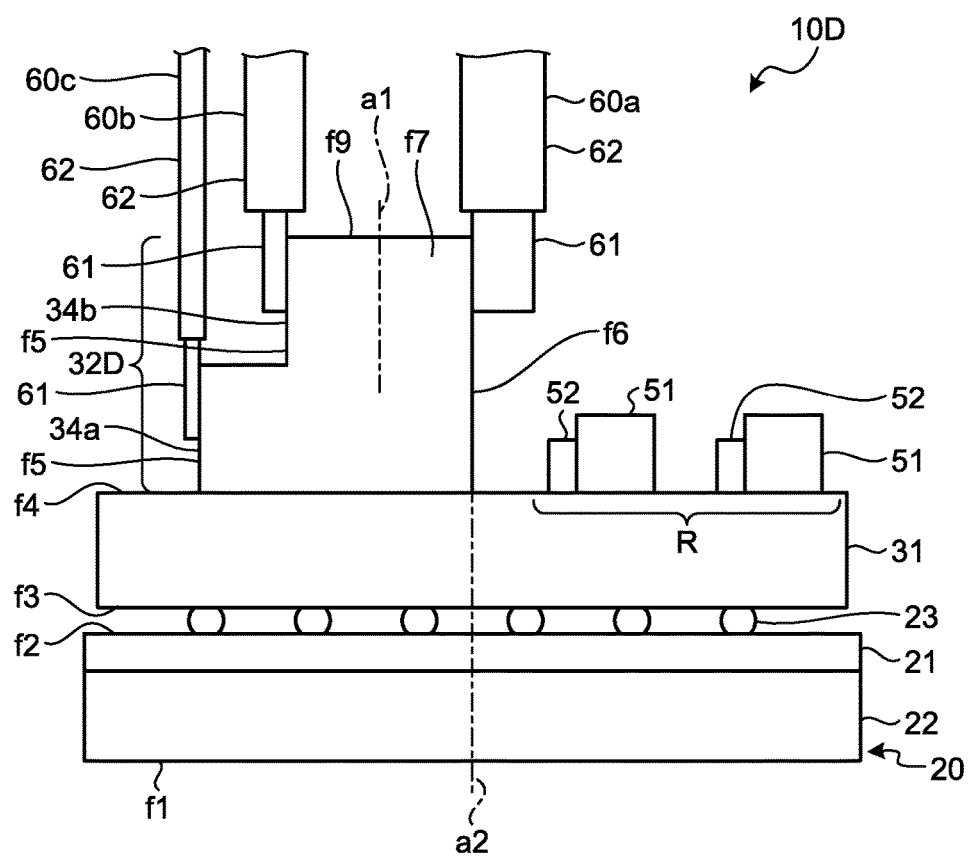
FIG. 15 is a side view of an imaging unit according to a first modification of the third embodiment.

Note that it is also possible to arrange the attachment portion 32C such that the side surface f6 of the attachment portion 32C overlaps with the center plane a2 of the side surfaces parallel to the side surfaces f5 and f6 of the attachment portion 32C of the semiconductor package 20, so as to further expand the electronic component mounting area R. FIG. 15 is a side view of an imaging unit 10D according to a first modification of the third embodiment.

In the imaging unit 10D, an attachment portion 32D is arranged such that the side surface f6 overlaps with the center plane a2 of the side surfaces parallel to the side surfaces f5 and f6 of the attachment portion 32D of the semiconductor package 20. This expands the electronic component mounting area R and allows more electronic components 51 and 52 to be mounted, making it possible to provide the imaging unit 10D having high functionality. Moreover, since the first step portion 34a and the second step portion 34b are provided on the side surface f5 of the attachment portion 32D, it is possible to increase the mounting density of the cables 60a to 60c. Furthermore, by connecting the cable 60a having a large diameter to the cable connection electrode 35a close to the center plane in the optical axis direction of the imaging unit 10D, it is possible to reduce the force applied to the imaging unit 10D generated by connecting the cables 60a to 60c to the cable connection electrodes 35a to 35c.

Figure 16:
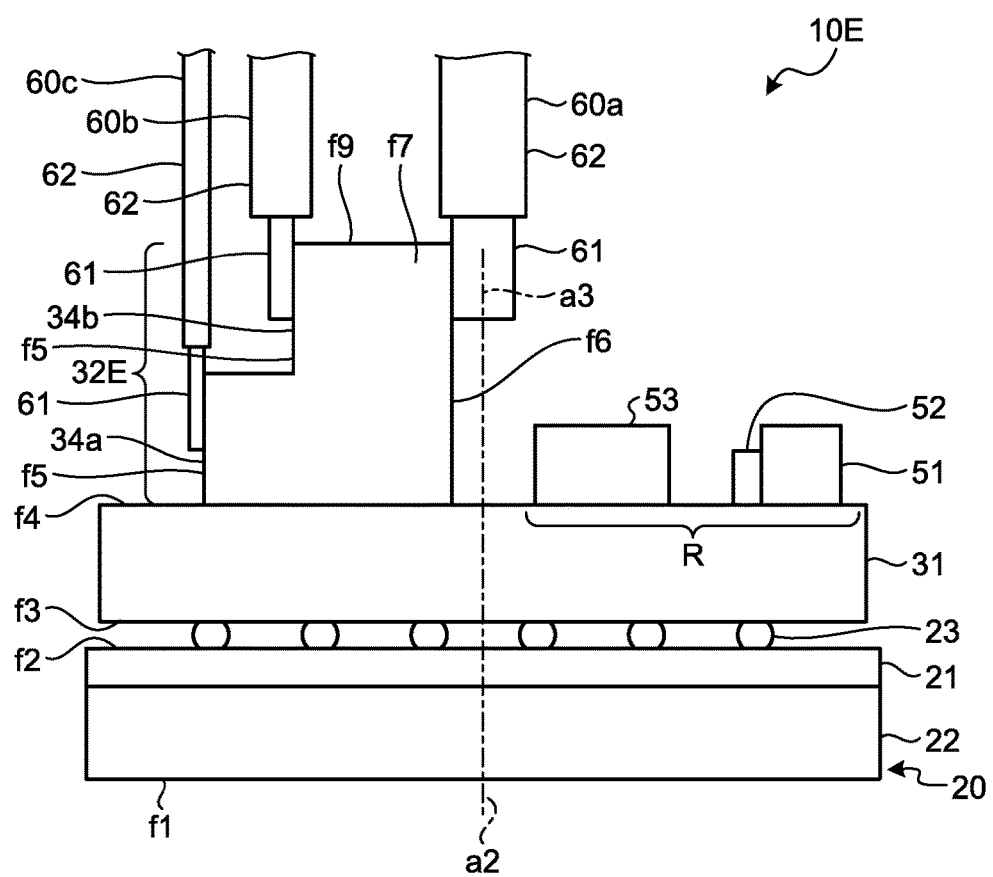
FIG. 16 is a side view of an imaging unit according to a second modification of the third embodiment.

Furthermore, the attachment portion 32C may be shifted until a center axis a3 of the cable 60a connected to the side surfaces f6 of the attachment portion 32C overlaps with the center plane a2 of the side surfaces parallel to the side surfaces f5 and f6 of the attachment portion 32C of the semiconductor package 20. FIG. 16 is a side view of an imaging unit 10E according to a second modification of the third embodiment.

In the imaging unit 10E, an attachment portion 32E is arranged such that the center axis a3 of the cable 60a connected to the cable connection electrode 35a formed on the side surface f6 of the attachment portion 32E overlaps with the center plane a2 of the side surfaces parallel to the side surfaces f5 and f6 of the attachment portion 32E of the semiconductor package 20. This further expands the electronic component mounting area R and allows a larger electronic component 53 to be amounted in addition to the electronic components 51 and 52, making it possible to provide the imaging unit 10E having high functionality. Moreover, the first step portion 34a and the second step portion 34b are provided on the side surface f5 of the attachment portion 32E, making it possible to increase the mounting density of the cables 60a to 60c. Furthermore, the center axis a3 of the cable 60a having a large diameter overlaps with the center plane a2 of the semiconductor package 20, making it possible to further reduce the force applied to the imaging unit 10E, generated by connecting the cables 60a to 60c to the cable connection electrodes 35a to 35c.

The imaging unit and the imaging module according to the present disclosure are useful in application to an endoscope system that demands an image with high image quality, reduction of diameter and length of the distal end portion.

According to the present disclosure, the attachment portion for connecting the cable is shifted from the center of the main body of the circuit board to allow an empty space to be used as an electronic component mounting area, making it possible to accurately supply the solder from above the electronic component mounting area. With this configuration, it is possible to mount a plurality of electronic components with high accuracy and simplicity while achieving miniaturization of an imaging unit.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An imaging unit comprising:
   a semiconductor package being a chip size package, the semiconductor package including:
      an image sensor, and
      a connection electrode formed on a back surface of the semiconductor package;
   a circuit board being accommodated in a projection plane in an optical axis direction of the semiconductor package, the circuit board including:
      a main body including a connection land formed on a front surface, the connection land being electrically and mechanically connected to the connection electrode via a bump, and
      an attachment portion protruding on a back surface of the main body and including cable connection electrodes formed on at least two opposing side surfaces among protruding side surfaces;
   a plurality of electronic components mounted on an electronic component mounting area on the back surface of the main body of the circuit board; and
   a plurality of cables electrically and mechanically connected to the cable connection electrodes of the attachment portion,
   wherein the attachment portion protrudes from the main body such that a center plane of the two side surfaces on which the cable connection electrodes are formed to oppose each other is shifted from a center plane of side surfaces of the semiconductor package which are parallel to the two side surfaces of the attachment portion, and at least one side surface is perpendicular to the back surface of the main body,
   the electronic component mounting area is arranged side-by-side with the attachment portion on a same plane as the attachment portion,
   each of the two opposing side surfaces of the attachment portion including the cable connection electrode formed thereon includes:
      a first step portion on the main body side; and
      a second step portion on the proximal end side in the optical axis direction of the image sensor; and
   the cable connection electrodes are formed on:
      a side surface of the second step portion on the electronic component mounting area side;
      a side surface of the second step portion opposing the side surface on the electronic component mounting area side; and
      the side surface of the first step portion opposing the side surface on the electronic component mounting area side.
2. The imaging unit according to claim 1,
   wherein the cable connection electrode formed in the first step portion is formed to separate from the main body, and the cable connection electrode formed in the second step portion is formed to separate from the first step portion, and the cable connection electrode formed in the first step portion is arranged so as to overlap with the electronic component in the optical axis direction.

3. The imaging unit according to claim 1, wherein grooves are formed at a portion between the main body and the first step portion and at a portion between the first step portion and the second step portion.

4. An imaging unit comprising:
a semiconductor package being a chip size package, the semiconductor package including:
an image sensor, and
a connection electrode formed on a back surface of the semiconductor package;
a circuit board being accommodated in a projection plane in an optical axis direction of the semiconductor package, the circuit board including:
a main body including a connection land formed on a front surface, the connection land being electrically and mechanically connected to the connection electrode via a bump, and
an attachment portion protruding on a back surface of the main body and including cable connection electrodes formed on at least two opposing side surfaces among protruding side surfaces;
a plurality of electronic components mounted on an electronic component mounting area on the back surface of the main body of the circuit board; and
a plurality of cables electrically and mechanically connected to the cable connection electrodes of the attachment portion,
wherein the attachment portion protrudes from the main body such that a center plane of the two side surfaces on which the cable connection electrodes are formed to oppose each other is shifted from a center plane of side surfaces of the semiconductor package which are parallel to the two side surfaces of the attachment portion, and at least one side surface is perpendicular to the back surface of the main body,
the electronic component mounting area is arranged side-by-side with the attachment portion on a same plane as the attachment portion,
the side surface of the attachment portion including the cable connection electrode formed thereon, opposing to the side surface on the electronic component mounting area side, includes a first step portion on the main body side and a second step portion on the proximal end side in the optical axis direction of the image sensor, and
the cable connection electrodes are formed on the first step portion and the second step portion on the side surface opposite to the side surface on the electronic component mounting area side, and on the side surface on the electronic component mounting area side.

5. The imaging unit according to claim 1,
wherein the plurality of cables includes a plurality of types of cables having different outer diameters, and
the cable having a larger outer diameter is connected to the cable connection electrode formed in the second step portion.

6. The imaging unit according to claim 4, wherein the side surface of the attachment portion on the electronic component mounting area side including the cable connection electrode formed thereon is within a vertical plane passing through a center plane of two side surfaces parallel to the two side surfaces of the attachment portion of the semiconductor package.

7. The imaging unit according to claim 4, wherein a center axis of the cable connected to the cable connection electrode formed on the side surface of the attachment portion on the electronic component mounting area side is positioned within a vertical plane passing through a center plane of side surfaces parallel to the two side surfaces of the attachment portion of the semiconductor package.

8. The imaging unit according to claim 1,
wherein a back surface of the attachment portion is parallel to a back surface of the semiconductor package, and
a marker indicating a center position of the semiconductor package is arranged on the back surface of the attachment portion.

9. The imaging unit according to claim 1, wherein the plurality of cables each of which connected to the circuit board and the cable connection electrode is accommodated in a projection plane in the optical axis direction of the semiconductor package.

10. An imaging module comprising:
a semiconductor package being a chip size package, the semiconductor package including:
an image sensor, and
a connection electrode formed on a back surface of the semiconductor package;
a circuit board being accommodated in a projection plane in an optical axis direction of the semiconductor package, the circuit board including:
a main body including a connection land formed on a front surface, the connection land being electrically and mechanically connected to the connection electrode via a bump, and
an attachment portion protruding on a back surface of the main body and including cable connection electrodes formed on at least two opposing side surfaces among the protruding side surfaces;
a plurality of electronic components mounted on an electronic component mounting area on the back surface of the main body of the circuit board,
wherein the attachment portion protrudes from the main body such that a center plane of the two side surfaces on which the cable connection electrodes are formed to oppose each other is shifted from a center plane of side surfaces of the semiconductor package which are parallel to the two side surfaces of the attachment portion, and the side surface is perpendicular to the back surface of the main body,
the electronic component mounting area is arranged side-by-side with the attachment portion on a same plane as the attachment portion;
each of the two opposing side surfaces of the attachment portion including the cable connection electrode formed thereon includes:
a first step portion on the main body side; and
a second step portion on the proximal end side in the optical axis direction of the image sensor; and
the cable connection electrodes are formed on:
a side surface of the second step portion on the electronic component mounting area side;
a side surface of the second step portion opposing the side surface on the electronic component mounting area side; and the side surface of the first step portion opposing the side surface on the electronic component mounting area side.

11. An endoscope apparatus comprising an insertion section including the imaging unit according to claim 1 provided at a distal end.

* * * * *